United States Patent [19]

Simons et al.

[11] 4,256,881
[45] Mar. 17, 1981

[54] BLOCKED BENZOTRIAZOLE COMPOUNDS AS DEVELOPMENT RESTRAINER PRECURSORS

[75] Inventors: Michael J. Simons, Ruislip; David T. Southby, West Harrow, both of England; Hans G. Ling, Rochester, N.Y.

[73] Assignee: Eastman Kodak Company, Rochester, N.Y.

[21] Appl. No.: 86,116

[22] Filed: Oct. 18, 1979

[30] Foreign Application Priority Data

Oct. 20, 1978 [GB] United Kingdom ............... 41437/78

[51] Int. Cl.³ .................. C07D 413/06; C07D 401/06
[52] U.S. Cl. .................................... 544/132; 546/199; 546/271; 548/261; 544/333; 544/366; 430/957; 430/544
[58] Field of Search ................ 548/261; 544/132, 333; 546/199, 271

[56] References Cited

U.S. PATENT DOCUMENTS

| | | |
|---|---|---|
| 3,260,597 | 7/1966 | Weyerts et al. |
| 3,265,498 | 8/1966 | Rogers et al. |
| 3,364,028 | 1/1968 | König et al. |
| 3,575,669 | 4/1971 | Haeff ............................ 331/94.5 |
| 3,649,267 | 3/1972 | Carlson et al. ...................... 96/3 |
| 3,732,238 | 5/1973 | Baker et al. ...................... 548/261 |
| 3,808,334 | 4/1974 | Dahle ............................ 548/261 |
| 3,856,520 | 12/1974 | Bloom et al. ...................... 96/3 |
| 3,893,859 | 7/1975 | Burness et al. ................... 96/61 R |
| 3,915,979 | 10/1975 | Chow et al. ...................... 548/261 |
| 4,038,403 | 7/1977 | Wright, Jr. ...................... 548/260 |
| 4,079,529 | 3/1978 | Jennen et al. ................... 38/102.2 |

FOREIGN PATENT DOCUMENTS 2282124 12/1976 France.
327204 7/1972 U.S.S.R. .................... 548/261

OTHER PUBLICATIONS

Hammond et al. Chem. Abst. 86: 63505q.
Research Disclosure, Mar. 1975, #13118.

Primary Examiner—John D. Randolph
Assistant Examiner—Jane T. Fan
Attorney, Agent, or Firm—Harold E. Cole

[57] ABSTRACT

Benzotriazole compounds employed as development restrainer precursors are described having on one nitrogen atom an alkali-hydrolyzable, N,N-disubstituted carbamoyl group. The compounds may have the following formula:

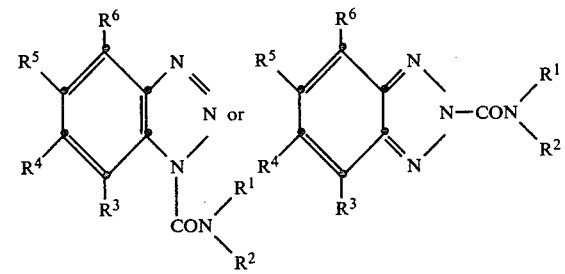

wherein:
$R^1$ and $R^2$ each represent a substituted or unsubstituted alicyclic, aliphatic, aromatic or heterocyclic moiety, or may be taken together with the nitrogen to which they are attached to form a heterocyclic ring; and $R^3$, $R^4$, $R^5$ and $R^6$ each represent hydrogen, nitro, lower alkyl, halogen, carbamoyl, sulfamoyl, RCONH— or $RSO_2NH$—, wherein R is lower alkyl or aryl.

4 Claims, No Drawings

BLOCKED BENZOTRIAZOLE COMPOUNDS AS DEVELOPMENT RESTRAINER PRECURSORS

This invention relates to certain benzotriazole compounds which are blocked with an alkali-hydrolyzable, N,N-disubstituted carbamoyl group. The compounds are employed as development restrainer precursors in color diffusion transfer photography.

U.S. Pat. No. 4,076,529 of Fleckenstein et al, issued Feb. 28, 1978, describes various color image transfer elements which employ nondiffusible, redox dye-releasing compounds which are alkali-cleavable upon oxidation to release a diffusible color-providing moiety. Development restrainers or precursors thereof are usually employed in such elements to try to progressively slow down the rate of development during the latter stages of the process without adversely affecting the initial development rate.

Various blocked antifoggants and development restrainers are disclosed in Japanese Pat. No. 586,882 and U.S. Pat. Nos. 3,364,028, 3,575,699 and 3,649,267. These references do not disclose the compounds of our invention, however.

*Research Disclosure* article 13118, March 1975, discloses various blocked benzotriazoles useful as development restrainers in color diffusion transfer elements. Such compounds have been found to become hydrolyzed by the alkaline processing composition too rapidly, however. In some instances, hydrolysis is essentially complete in ten seconds or less. When that happens, the initial development rate is adversely affected.

The compounds employed in our invention hydrolyze at a much slower rate than those of the prior art. In a 0.1 M aqueous sodium hydroxide solution, our compounds typically have a half-life of ten seconds to several minutes. These compounds have the desired property of progressively restraining development without adversely affecting the initial development rate.

A benzotriazole compound in accordance with our invention has on one of its nitrogen atoms an alkalihydrolyzable, N,N-disubstituted carbamoyl group.

In a preferred embodiment of our invention, the benzotriazole compound has either of the following formulas:

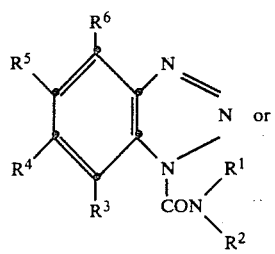

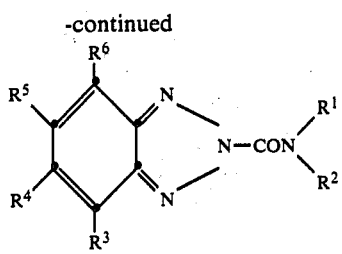

wherein:

$R^1$ and $R^2$ each represent a substituted or unsubstituted alicyclic, aliphatic, aromatic or heterocyclic moiety, or may be taken together with the nitrogen to which they are attached to form a heterocyclic ring; and $R^3$, $R^4$, $R^5$ and $R^6$ each represent hydrogen, nitro, lower alkyl (including substituted alkyl) of 1 to 6 carbon atoms, such as methyl, ethyl, propyl, isopropyl, hexyl, carboxymethyl, etc; halogen, such as chloro, bromo, etc; carbamoyl, sulfamoyl, $RCONH-$ or $RSO_2NH-$, wherein R is a lower alkyl group of 1 to 6 carbon atoms, such as methyl, ethyl, propyl, isopropyl, hexyl, carboxymethyl, etc, or an aryl group of 6 to 10 carbon atoms, such as phenyl, tolyl, etc.

In the above formulas, $R^1$ and $R^2$ can each be a substituted or unsubstituted alicyclic group, such as cycloalkyl of 3 to 20 carbon atoms; e.g., cyclopropyl, cyclohexyl, cyclodecyl or cyclooctadecyl; an aliphatic group, such as a straight or branched chain alkyl group of 1 to 20 carbon atoms, including aralkyl and aryloxyalkyl, e.g., methyl, ethyl, isopropyl, butyl, hydroxyethyl, octyl, pentyl, dodecyl, pentadecyl, octadecyl, benzyl, furfuryl, or phenoxypropyl; an aromatic group, such as aryl of 6 to 20 carbon atoms, including alkaryl and alkoxyaryl, e.g., phenyl, naphthyl, methylphenyl, 4-methoxyphenyl, p-sulfamoylphenyl, p-dodecylphenyl, butoxyphenyl; or a heterocyclic moiety containing from 5 to 20 non-metallic atoms, such as thienyl, pyridyl or pyrimidyl; or may be taken together with the nitrogen to which they are attached to form a heterocyclic ring, such as morpholine, piperidine, pyrrolidine, piperazine, etc. In a preferred embodiment of the invention, each $R^1$ and $R^2$ is a substituted or unsubstituted alkyl or aryl group, as described above. In a more preferred embodiment, each $R^1$ and $R^2$ is ethyl, phenyl, 4-methoxyphenyl or $-(CH_2)_{10}-COOC_2H_5$, or are taken together to complete a morpholine or piperidine ring. In another more preferred embodiment of this invention, $R^3$, $R^4$ and $R^6$ are each hydrogen, and $R^5$ is methyl.

Typical compounds included within the scope of the above formulas include the following:

Compound 1

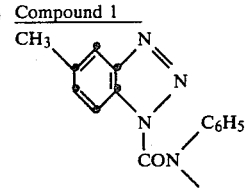

Compound 2

-continued
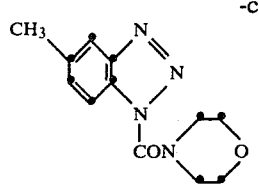
Compound 3
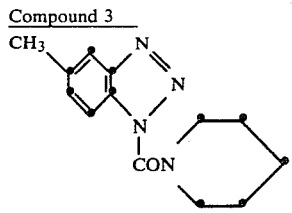
Compound 4
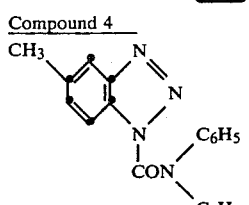
Compound 5
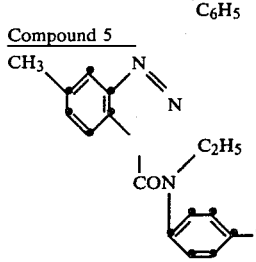
Compound 6
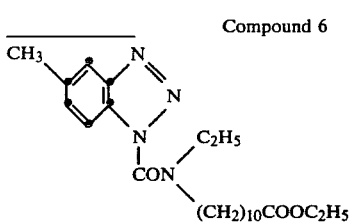
Compound 7
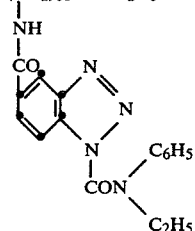
Compound 8
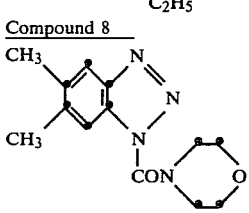
Compound 9
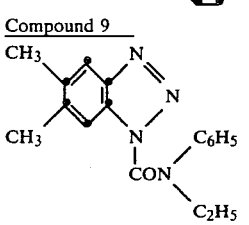
-continued
Compound 10
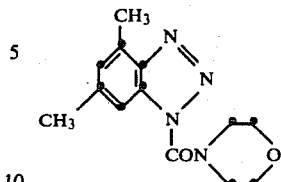
Compound 11
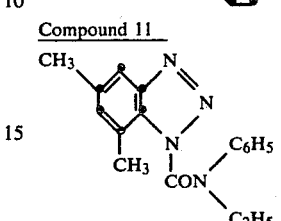
Compound 12
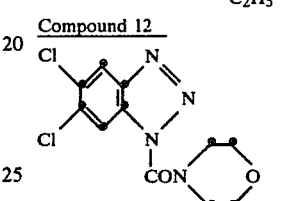
Compound 13
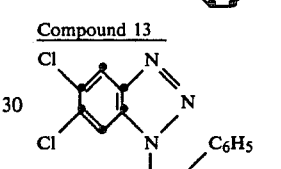
Compound 14
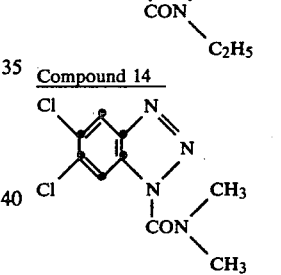
Compound 15
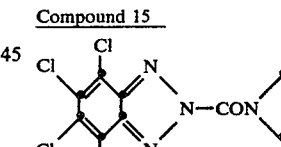
Compound 16
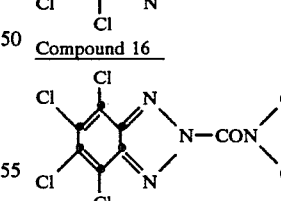
Compound 17
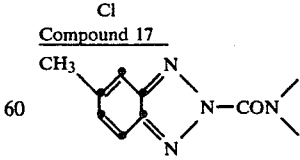
Compound 18
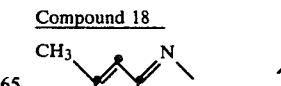
Compound 19

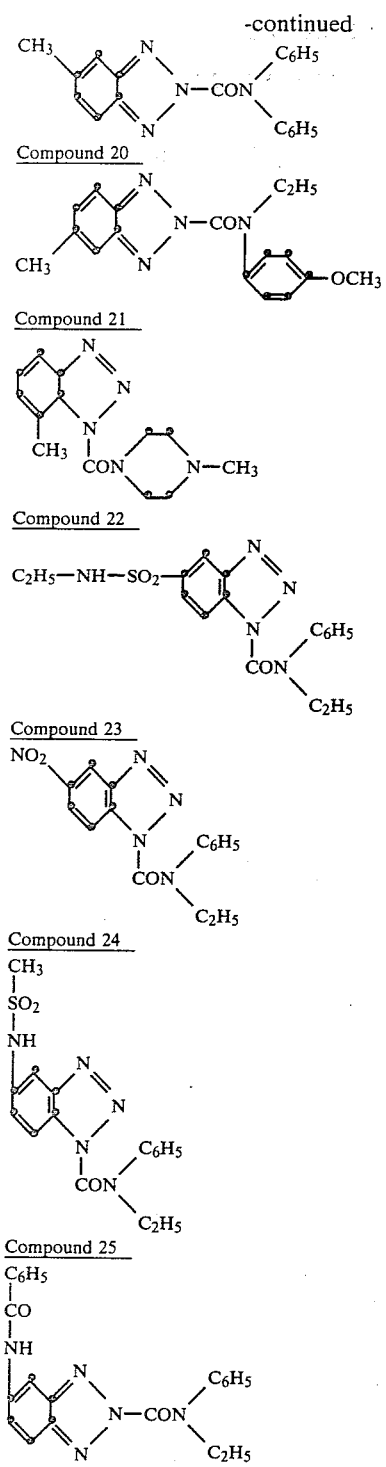

Compound 20

Compound 21

Compound 22

Compound 23

Compound 24

Compound 25

The development restrainer precursors of this invention may be incorporated into any layer of a photographic element or assemblage. They may be incorporated into a silver halide emulsion layer, a dye image-providing material layer, a dye image-receiving layer, interlayers, etc. They may be employed in any amount suitable for the intended purpose. In general, good results are obtained when the compounds are employed in a concentration range of from 0.05 to 1.5 grams per square meter of element. The compounds may be incorporated as solutions, as fine particulate dispersions, or dissolved in droplets of a high-boiling solvent.

Various photographic elements, film assemblages, receiving elements, cover sheets and color diffusion transfer processes in which our compounds can be employed are described more fully in our copending U.S. Application Ser. No. 085,944, entitled "Development Restrainer Precursors for Photographic Elements", filed of even date herewith, the disclosure of which is hereby incorporated by reference.

During photographic processing, the carbamoyl substituent is split off of the compounds of our invention to provide the development restrainer, i.e., a compound according to Formulas I and II above is hydrolyzed by aqueous alkaline processing composition to form the development restrainer:

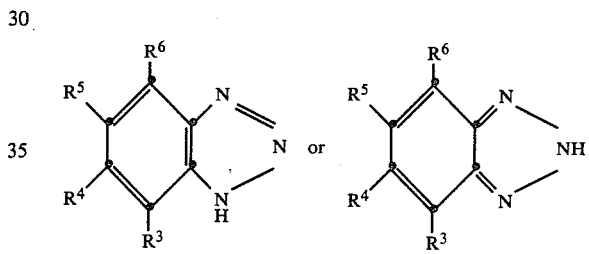

wherein:

$R^3$, $R^4$, $R^5$ and $R^6$ are defined as above, which may be ionized in the composition.

The following examples are provided to further illustrate the invention.

EXAMPLE 1

Preparation of Compound 1

Compound 1:
1-(N-Ethyl-N-phenylcarbamoyl)-5-methylbenzotriazole

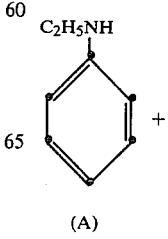

(A)

-continued

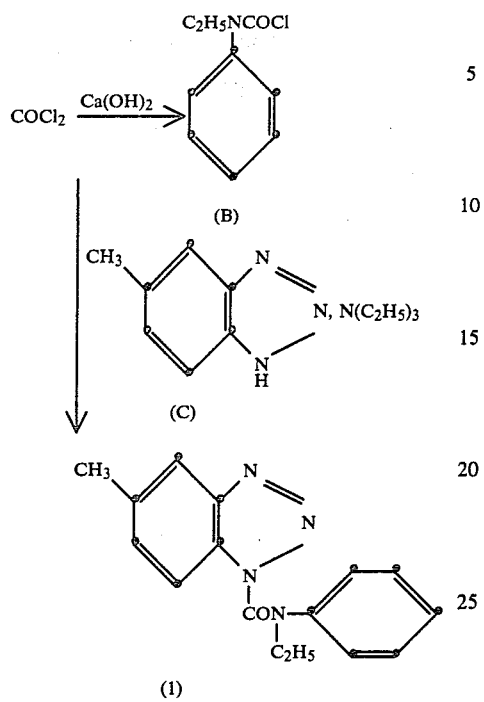

(a) N-Ethyl-N-phenylcarbamoyl chloride (B)

This was prepared by the method of Carpino and Gowecke (L. A. Carpino and S. Gowecke, *J. Org. Chem.*, 29, 2824, 1964), in 60 percent yield, m.p. 44° to 45° C. (uncorr.).

(b)
1-(N-Ethyl-N-phenylcarbamoyl)-5-methylbenzotriazole (1)

5-Methylbenzotriazole (C) (13.3 g, 0.1 mole) was suspended in triethylamine (100 ml) and N-ethyl-N-phenylcarbamoyl chloride (B) (18.35 g, 0.1 mole) was added in small portions, with stirring. The resultant mixture was heated under reflux for 2 hours, cooled, and the solvent was removed under reduced pressure. The residue was taken up in water (200 ml) and dichloromethane (200 ml) and the organic layer was separated. This was washed with dilute hydrochloric acid (3 molar, 1×200 ml), dried (magnesium sulfate) and the solvent was removed to leave an oil which crystallized from a cyclohexane:petroleum ether (b.p. 40° to 60° C.) mixture (1:1.5 v/v) to give a colorless solid (21.72 g, 78 percent), m.p. 42° to 43° C. (uncorr.), which is (1) and the 6-methyl isomer.

$C_{16}H_{16}N_4O$ Requires: C, 68.55; H, 5.75; N, 19.99%; Found: C, 68.11; H, 5.81; N, 19.86%.

EXAMPLE 2

Preparation of Compound 2

Compound 2:
1-(N-Morpholinocarbonyl)-5-methylbenzotriazole

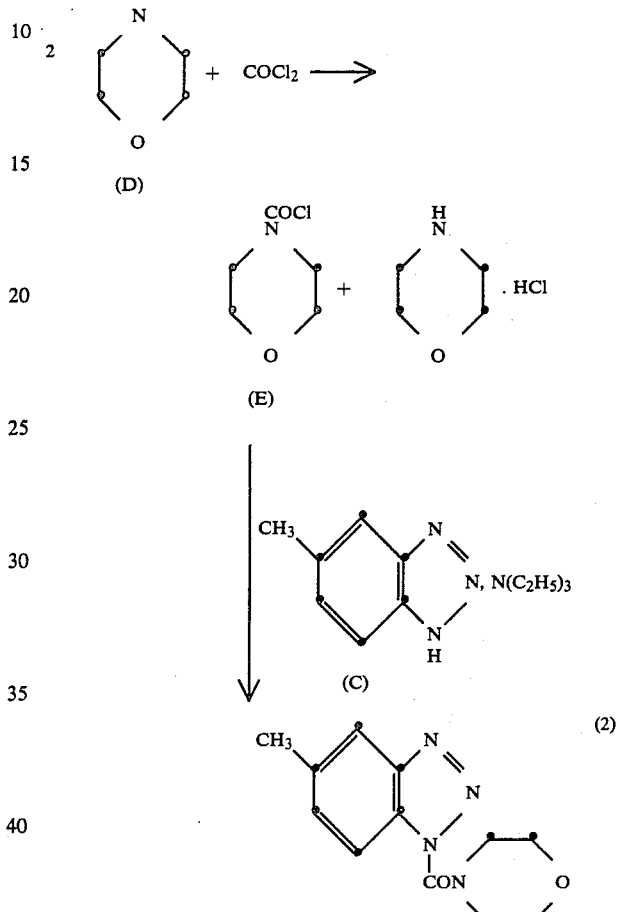

(a) Morpholinocarbonyl chloride (E)

This was prepared by the method of Boon (W. R. Boon, J.C.S., 307, 1947), in 66 percent yield, b.p. 105° to 107° C./7.5 mm.

(b) 1-Morpholinocarbonyl-5-methylbenzotriazole (2)

Compound 2 was prepared by treating 5-methylbenzotriazole (C) (8.89 g, 67 m.mole) with morpholinocarbamoyl chloride (E) (10 g, 67 m.mole) in a manner similar to that described in the preparation of (1). The product which included the 6-methyl isomer, was crystallized from methanol (100 ml). Yield, 13.2 g, 81 percent, m.p. 81° to 82° C. (uncorr.).

$C_{12}H_{14}N_4O_2$ Requires: C, 58.52; H, 5.73; N, 22.75%; Found: C, 58.33; H, 5.73; N, 22.97%.

Other examples which were prepared via the method used for Compound 2 include:

EXAMPLE 3

Preparation of Compound 3

Compound 3: 1-Piperidinocarbonyl-5-methylbenzotriazole

This was prepared in 73 percent yield, (including the 6-methyl isomer), m.p. 49° to 50° C. (uncorr.) from petroleum ether (b.p. 40° to 60° C.).

$C_{13}H_{16}N_4O$ Requires: C, 63.91; H, 6.60; N, 22.94%; Found: C, 63.53; H, 6.60; N, 22.87%.

EXAMPLE 4

Preparation of Compound 4

Compound 4: 1-(N,N-diphenylcarbamoyl)-5-methylbenzotriazole

This was prepared in 76 percent yield, (including the 6-methyl isomer), m.p. 132° to 133° C. (uncorr., from methanol).

$C_{20}H_{16}N_4O$ Requires: C, 73.15; H, 4.91; N, 17.06%; Found: C, 72.85; H, 5.03; N, 17.28%.

EXAMPLE 5

Preparation of Compound 8

Compound 8: 1-Morpholinocarbonyl-5,6-dimethylbenzotriazole

This was prepared in 61 percent yield, m.p. 191° C. (uncorr., from methanol). $C_{13}H_{16}N_4O_2$ Requires: C, 59.99; H, 6.20; N, 21.53%; Found: C, 59.82; H, 6.20; N, 22.27%.

EXAMPLE 6

Preparation of Compound 10

Compound 10: 1-Morpholinocarbonyl-4,6-dimethylbenzotriazole

This was prepared in 64 percent yield including the 5,7-dimethyl isomer, m.p. 115° C. (uncorr., from methanol).

$C_{13}H_{16}N_4O_2$ Requires: C, 59.99; H, 6.20; N, 21.53%; Found: C, 59.10; H, 6.12; N, 21.77%.

EXAMPLE 7

Preparation of Compound 12

Compound 12: 1-Morpholinocarbonyl-5,6-dichlorobenzotriazole

This was prepared in 64 percent yield, m.p. 145° C. (uncorr., from methanol).

$C_{11}H_{10}Cl_2N_4O_2$ Requires: C, 43.87; H, 3.35; Cl, 23.54; N, 18.61%; Found: C, 43.75; H, 3.40; Cl, 24.76; N, 18.80%.

EXAMPLE 8

Preparation of Compound 15

Compound 15: 2-Morpholinocarbonyl-4,5,6,7-tetrachlorobenzotriazole

This was prepared in 50 percent yield, m.p. 194° C. (uncorr., from methanol).

$C_{11}H_8Cl_4N_4O_2$ Requires: C, 35.71; H, 2.18; Cl, 38.32; N, 15.14%; Found: C, 35.64; H, 2.17; Cl, 38.00; N, 15.50%.

EXAMPLE 9

Preparation of Compound 6

Compound 6: Ethyl-11-[N-(5-methyl-1-benzotriazolylcarbonyl)-N-ethyl]aminoundecanoate This was prepared in 88 percent yield (including the 6-methyl isomer), as an oil after chromatographic purification.

$C_{23}H_{36}N_4O_3$ Requires: C, 66.32; H, 8.71; N, 13.45%; Found: C, 66.26; H, 8.62; N, 13.55%.

Other compounds which were prepared in two stages via the method used for compound 1 include:

EXAMPLE 10

Preparation of Compound 5

Compound 5: 1-(N-Ethyl-N-(4-methoxyphenyl)-5-methylbenzotriazole

This was prepared in 67 percent yield, (including the 6-methyl isomer), m.p. 75° C. (uncorr., from cyclohexane:petroleum ether) (40° to 60° C.) (1:4).

$C_{17}H_{18}N_4O_2$ Requires: C, 65.79; H, 5.85; N, 18.05; Found: C, 65.45; H, 5.92; N, 17.93.

EXAMPLE 11

Preparation of Compound 9

Compound 9: 1-(N-Ethyl-N-phenylcarbamoyl)-5,6-dimethylbenzotriazole

This was prepared in 81 percent yield, m.p. 136° C. (uncorr., from methanol).

$C_{17}H_{18}N_4O$ Requires: C, 69.37; H, 6.16; N, 19.04%; Found: C, 69.12; H, 6.21; N, 19.28%.

EXAMPLE 12

Preparation of Compound 11

Compound 11: 1-(N-Ethyl-N-phenylcarbamoyl)-5,7-dimethylbenzotriazole

This was prepared in 71 percent yield, (including the 4,6-dimethyl isomer), m.p. 90° C. (uncorr., from methanol).

$C_{17}H_{18}N_4O$ Requires: C, 69.37; H, 6.16; N, 19.04%; Found: C, 69.33; H, 6.20; N, 19.48%.

EXAMPLE 13

Preparation of Compound 13

Compound 13: 1-(N-Ethyl-N-phenylcarbamoyl)-5,6-dichlorobenzotriazole

This was prepared in 88 percent yield, m.p. 120° C. (uncorr., from cyclohexane).

$C_{15}H_{12}Cl_2N_4O$ Requires: C, 53.75; H, 3.61; Cl, 21.15; N, 16.72%; Found: C, 53.79; H, 3.74; Cl, 21.18; N, 16.92%.

EXAMPLE 14

Preparation of Compound 16

Compound 16:
2-(N-Ethyl-N-phenylcarbamoyl)-4,5,6,7-tetra-chlorobenzotriazole

This was prepared in 86 percent yield, m.p. 157° C. (uncorr., from cyclohexane).

$C_{15}H_{10}Cl_4N_4O$ Requires: C, 44.59; H, 2.49; Cl, 35.09; N, 13.87%; Found: C, 44.65; H, 2.50; Cl, 35.18; N, 14.15%.

EXAMPLE 15

Preparation of Compound 7

Compound 7: Ethyl 11-[1-(N-Ethyl-N-phenylcarbamoyl)-6-benzo-triazolecarbonamido]undecanoate This was prepared in 87 percent yield as a white oily solid after chromatographic purification.

$C_{29}H_{39}N_5O_4$ Requires: C, 66.28; H, 7.48; N, 13.32%; Found: C, 66.77; H, 7.54; N, 13.42%.

EXAMPLE 16

Preparation of Compound 14

Compound 14:
5,6-Dichloro-1-dimethylcarbamoylbenzotriazole

In 100 ml of dry tetrahydrofuran, 1.2 g of sodium hydride is suspended. To this mixture, a solution of 9.4 g of 5,6-dichlorobenzotriazole in 250 ml of tetrahydrofuran is added with vigorous stirring. After it is stirred at room temperature for 30 minutes, 5.4 g of N,N-dimethylcarbamoyl chloride is added, and the reaction mixture is refluxed for 15 minutes, then allowed to gradually come to room temperature. The sodium chloride salt formed is removed; the solution is treated with charcoal and filtered. The solvent is evaporated to yield a white, solid residue. Recrystallization from aqueous methanol yields 6.7 g (51.9 percent) of colorless solid; m.p. 120° to 123° C.

$C_9H_8Cl_2N_4O$ Requires: C, 41.7; H, 3.1; N, 21.7; Found: C, 42.2; H, 3.3; N, 21.6.

EXAMPLE 17

The rates of hydrolysis of the development restrainer precursors in alkaline solution were estimated as follows:

A silver-silver chloride electrode was freshly prepared by electrolysis of a clean silver rod in 0.5 M aqueous potassium chloride solution. This electrode, together with a standard calomel reference electrode, was connected to a pH meter whose output was recorded on a chart recorder. The electrodes were immersed in a stirred solution at room temperature of composition: 10 percent v/v ethanol, 90 percent water, 0.1 M sodium hydroxide, and 0.01 M potassium chloride. The volume of the solution was 50 ml. A solution of development restrainer precursor (2 ml of 0.4 M solution in ethanol) was added rapidly from a syringe, and the resulting perturbation of the electrical potential given by the electrode pair was recorded as a function of time. When 5-methylbenzotriazole was added, the time taken for the potential to reach 60 percent of the difference between the final and initial readings (which should approximately correspond to 50 percent adsorption of the benzotriazole at the electrode) was about 3 seconds. This is taken as the response time of the measuring system.

In this way, estimates were made of the $t_{\frac{1}{2}}$ value (time for half the added development restrainer precursor to be hydrolyzed to the development restrainer) for the various compounds of the invention. The values found are given in Table I. The letter I by a value indicates that the compound was largely insoluble in the solution, giving a greater $t_{\frac{1}{2}}$ value than would otherwise be the case.

TABLE I

| Compound No. | Hydrolysis $t_{\frac{1}{2}}$ (seconds) |
|---|---|
| 1 | >300 I |
| 2 | 15 |
| 3 | 65 |
| 4 | >300 I |
| 5 | >300 I |
| 6 | >300 I |
| 7 | >300 I |
| 8 | 11 |
| 9 | >300 I |
| 10 | 9 |
| 11 | >300 I |
| 12 | 30 I |
| 13 | >300 I |
| 15 | 180 I |
| 16 | >600 I |

EXAMPLE 18

Photographic Test (i) Preparation of receiver sheets (a) A receiver sheet was prepared by coating an aqueous solution (pH 6.5) onto polyethylene-coated paper to give the following coated layer (concentrations are in grams per square meter unless otherwise stated):

| | |
|---|---|
| gelatin | 2.2 |
| polyvinylimidazole (10 percent quaternized with 2-chloroethanol) | 2.2 |
| 4-hydroxymethyl-4-methyl-1-phenyl-3-pyrazolidone | 0.22 |
| piperidine hydrochloride | 0.09 |
| formaldehyde | 0.04 |

This receiver (a) constitutes a control.

(b) Another receiver was prepared as (a), but with the addition of a fine dispersion of prior art compound [1-cyclohexylcarbamoyl-5(6)-methylbenzotriazole] (0.27) dissolved in droplets of diethyl lauramide (0.79).

(c) Another receiver was prepared similar to (a), but with the addition of a solution in acetone of Compound 1 (0.48) of the invention.

(d) Another receiver was prepared similar to (a), but with the addition of a solution, in tetrahydrofuran, of Compound 2 (0.32) of the invention.

(ii) Preparation of Photosensitive Element

A photosensitive element was prepared by coating the following layers in the order recited on a poly(ethylene terephthalate) film support. Quantitites are parenthetically given in grams per square meter unless otherwise stated.

(1) red-sensitive, negative-working, 15:85 silver chlorobromide emulsion (silver 0.59, gelatin 1.35) and cyan RDR A (0.44) dispersed in 1,4-cyclohexylenedimethylene-bis-(2-ethylhexanoate) (0.22);

(2) interlayer of gelatin (1.35) and 2,5-di-sec-dodecylhydroquinone (0.97);

(3) magenta RDR B (0.44) dispersed in 1,4-cyclohexylenedimethylene-bis(2-ethylhexanoate) (0.22) and gelatin (1.35);

(4) green-sensitive, negative-working, 15:85 silver chlorobromide emulsion (silver 0.95, gelatin 1.35);

(5) interlayer of gelatin (1.35) and 2,5-di-sec-dodecylhydroquinone (0.83);

(6) yellow RDR C (1.12) dispersed in 1,4-cyclohexylenedimethylene-bis(2-ethylhexanoate) (0.56), gelatin (1.43), and bis(vinylsulfonylmethyl) ether (0.11);

(7) blue-sensitive, negative-working, 15:85 silver chlorobromide emulsion (silver 1.18, gelatin 1.35) and 2,5-di-sec-dodecylhydroquinone (0.1); and (8) gelatin (1.35) and copoly[styrene(N,N-dimethyl-N-benzyl-N-3-maleimidopropyl)ammonium chloride] (0.1).

CYAN RDR A

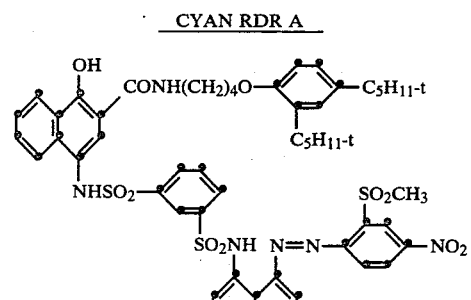

MAGENTA RDR B

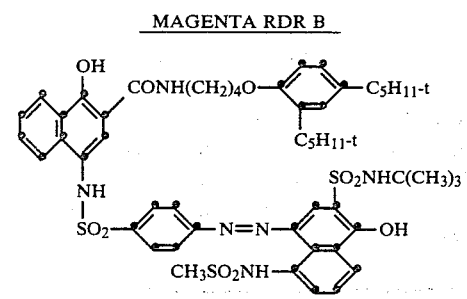

YELLOW RDR C

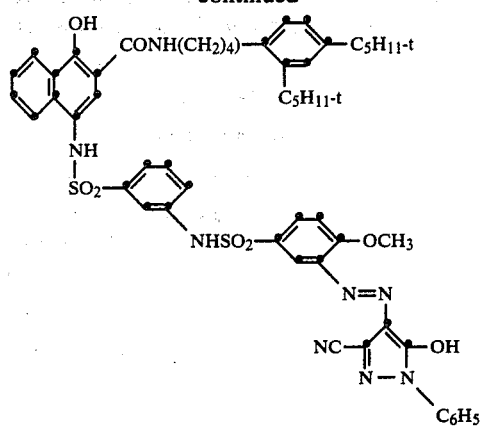

(iii) Testing of Receiver Sheets

Portions of the photosensitive element of (ii) were exposed to a sensitometric light source. They were soaked in the activator solution described below at 30° C. for 15 seconds, then withdrawn and squeegeed into intimate face-to-face contact with a portion of the receiver sheet of (i).

| Activator Solution | |
|---|---|
| potassium hydroxide | 37 g |
| benzyl alcohol | 10 ml |
| 11-aminoundecanoic acid | 2 g |
| 6-aminohexanoic acid | 15 g |
| 5-methylbenzotriazole | 1 g |
| water to | 1 liter |

The coatings were peeled apart after 2.5 and 5 minutes process time. A negative dye image was visible on the receiving sheets. The reflection densities in unexposed ($D_{min}$) and in fully exposed ($D_{max}$) areas were read through red, green and blue filters. The results are given in Table II. Δ signifies the difference between the density at 5 minutes and the density at 2.5 minutes.

TABLE II

| Receiver | Development Restrainer | Time (minutes) | $D_{min}$ | | | $D_{max}$ | | |
|---|---|---|---|---|---|---|---|---|
| | | | Red | Green | Blue | Red | Green | Blue |
| (a) control | None | 2.5 | 0.11 | 0.15 | 0.18 | 2.51 | 2.19 | 2.78 |
| | | 5 | 0.18 | 0.20 | 0.30 | 2.57 | 2.24 | 3.20 |
| | | Δ | 0.07 | 0.05 | 0.12 | 0.08 | 0.05 | 0.42 |
| (b) control | prior art compound | 2.5 | 0.12 | 0.16 | 0.19 | 2.08 | 1.78 | 2.38 |
| | | 5 | 0.16 | 0.18 | 0.24 | 2.68 | 2.06 | 2.74 |
| | | Δ | 0.04 | 0.02 | 0.05 | 0.60 | 0.28 | 0.36 |
| (c) | Compound 1 | 2.5 | 0.13 | 0.17 | 0.16 | 2.29 | 2.09 | 2.17 |
| | | 5 | 0.16 | 0.20 | 0.21 | 2.56 | 2.17 | 2.41 |
| | | Δ | 0.03 | 0.03 | 0.05 | 0.27 | 0.08 | 0.24 |
| (d) | Compound 2 | 2.5 | 0.12 | 0.15 | 0.16 | 2.56 | 2.20 | 2.34 |
| | | 5 | 0.18 | 0.18 | 0.21 | 3.16 | 2.42 | 2.87 |
| | | Δ | 0.06 | 0.03 | 0.05 | 0.60 | 0.28 | 0.53 |

The results show that all of the development restrainer precursors limited the growth of minimum density compared with control (a). However, the rapid release of the prior art compound resulted in undue suppression of the red and green $D_{max}$ at the shorter time of lamination. The compounds of the invention, however, gave similar control of $D_{min}$ without so much suppression of $D_{max}$.

EXAMPLE 19

Photographic Test (i) Preparation of Receiver Sheets (e) A receiver sheet was prepared by separately coating and drying the following aqueous solutions (pH 5.5) on polyethylene coated paper (concentrations are in grams per square meter unless otherwise stated):

| Layer 1 | |
|---|---|
| gelatin | 2.2 |
| formaldehyde | 0.03 |

| Layer 2 | |
|---|---|
| polyvinylimidazole (10 percent quaternized with 2-chloroethanol) | 2.2 |
| 4-hydroxymethyl-4-methyl-1-phenyl-3-pyrazolidone | 0.22 |
| formaldehyde | 0.03 |

This receiver (e) constitutes a control.

(f) Another receiver was prepared similar to (e), except that Layer 1 was:

| | |
|---|---|
| gelatin | 2.2 |
| formaldehyde | 0.03 |
| Compound 1 | 0.81 |
| N-n-butylacetanilide | 1.6 |
| Aerosol OT (trademark) surfactant | 0.07 |

(ii) Preparation of Photosensitive Element

A photosensitive element was prepared by coating the following layers in the order recited on a poly(ethylene terephthalate) film support. Quantitites are parenthetically given in grams per square meter unless otherwise stated:

(1) cyan dye-providing layer of gelatin (1.5), cyan RDR D (0.45) dispersed in N,N-diethyl-lauramide (0.22), and bis(vinylsulfonylmethyl)ether (0.03);

(2) red-sensitive, direct-positive, 0.75 μm silver bromide emulsion (silver 0.35, gelatin 1.0), 1-dimethyl-3-[4-(2-formylhydrazino)phenyl]thiourea (10 mg/silver mol);

(3) interlayer of gelatin (1.0) and 2,4-di-sec-dodecylhydroquinone (0.5);

(4) magenta dye-providing layer of magenta RDR E (0.45) dispersed in N,N-diethyl-lauramide (0.22), gelatin (1.0) and bis(vinylsulfonylmethyl)ether (0.03);

(5) green-sensitive, direct-positive, 0.75 μm silver bromide emulsion (silver 0.35, gelatin 1.0), 1-methyl-3[4-(2-formylhydrazino)phenyl]thiourea (25 mg/silver mol);

(6) interlayer of gelatin (1.0) and 2,5-di-sec-dodecylhydroquinone (0.5);

(7) yellow dye-providing layer of yellow RDR F (0.5) dispersed in N,N-diethyl-lauramide (0.25), gelatin (1.0) and bis(vinylsulfonylmethyl)ether (0.03);

(8) blue-sensitive, direct-positive, 0.75 μm silver bromide emulsion (silver 0.35, gelatin 1.0), 1-methyl-3[4-(2-formylhydrazino)phenyl]thiourea (15 mg/silver mol); and (9) overcoat layer of gelatin (1.0) and copoly[styrene-(N,N-dimethyl-N-benzyl-N-3-maleimidopropyl)ammonium chloride] (0.05).

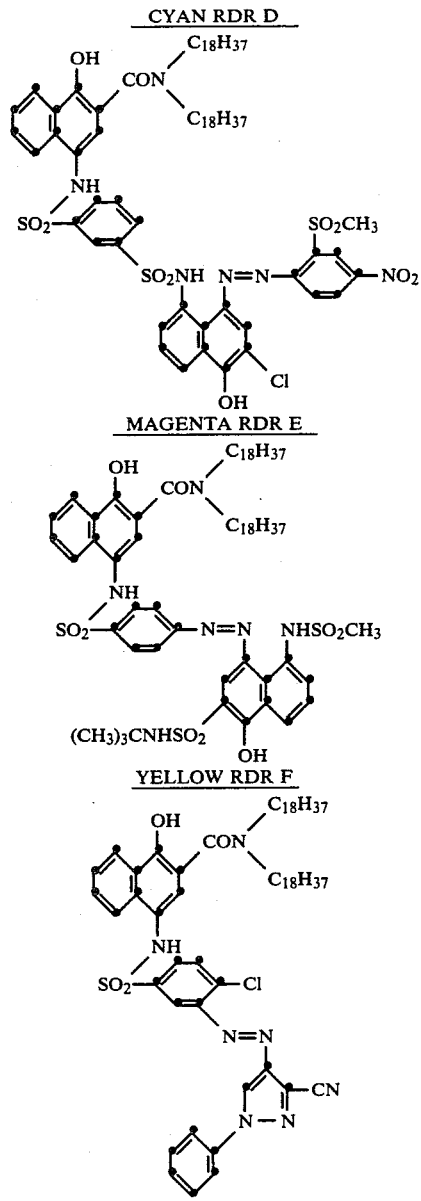

(iii) Testing of Receiver Sheets

Portions of the photosensitive element of (ii) were exposed to a sensitometric light source. They were soaked in the activator solution described below at 28° C. for 30 seconds, then withdrawn and squeegeed into intimate face-to-face contact with a portion of the receiver sheets of (i).

| Activator Solution | |
|---|---|
| potassium hydroxide | 42 g |

| Activator Solution | |
|---|---|
| benzyl alcohol | 10 ml |
| 5-methylbenzotriazole | 3 g |
| water to | 1 liter |

The coatings were peeled apart after 3.5 and 6 minutes at 21° C. A positive dye image was visible on the receiving sheets. The image was measured with a reflection densitometer through red, green and blue filters. In Table III are listed $D_{min}$ and speed values (speed equals—relative $Log_{10}$ exposure).

TABLE III

| Receiver | Development Restrainer | Time (minutes) | $D_{min}$ Red | Green | Blue | Speed Red | Green | Blue |
|---|---|---|---|---|---|---|---|---|
| (e) | None | 3.5 | 0.46 | 0.27 | 0.33 | 1.46 | 1.80 | 1.07 |
| | | 6 | 0.53 | 0.30 | 0.37 | 1.43 | 1.71 | 1.02 |
| | | Δ | 0.07 | 0.03 | 0.04 | −0.03 | −0.09 | −0.05 |
| (f) | Compound 1 | 3.5 | 0.46 | 0.27 | 0.35 | 1.47 | 1.82 | 1.06 |
| | | 6 | 0.30 | 0.30 | 0.37 | 1.46 | 1.86 | 1.07 |
| | | Δ | 0.04 | 0.03 | 0.02 | −0.01 | +0.04 | +0.01 |

The results show that the compound of the invention had the desired effect of minimizing sensitometric changes as the processing time was increased from 3.5 to 6 minutes.

The invention has been described in detail with particular reference to preferred embodiments thereof, but it will be understood that variations and modifications can be effected within the spirit and scope of the invention.

What is claimed is:

1. A compound having either of the following formulas:

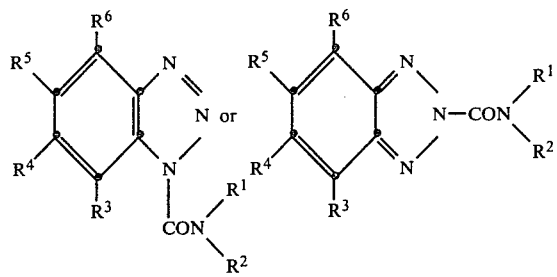

wherein:

$R^1$ and $R^2$ together complete a morpholine ring or a piperidine ring; and $R^3$, $R^4$, $R^5$ and $R^6$ each represent hydrogen, nitro, lower alkyl, halogen, carbamoyl, sulfamoyl, $RCONH-$, or $RSO_2NH-$, wherein R is lower alkyl or aryl of 6 to 10 carbon atoms.

2. The compound of claim 1 wherein $R^1$ and $R^2$ together complete a morpholine ring.

3. The compound of claim 1 wherein $R^1$ and $R^2$ together complete a piperidine ring.

4. The compound of claim 1 having the formula:

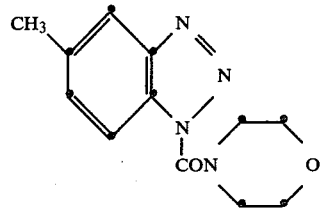

* * * * *